United States Patent
Yuan et al.

(10) Patent No.: US 6,589,480 B1
(45) Date of Patent: Jul. 8, 2003

(54) METHOD FOR SANITIZING A FOOD PROCESSING ENVIRONMENT

(75) Inventors: James T. C. Yuan, Naperville, IL (US); Edward F. Steiner, Lombard, IL (US)

(73) Assignees: L'Air Liquide - Societe Anonyme a'Directoire et Conseil de Surveillance pour l'Etude et l'Exploitation des Procedes Georges Claude, Paris (FR); American Air Liquide, Inc., Fremont, CA (US)

( * ) Notice: Subject to any disclaimer, the term of this patent is extended or adjusted under 35 U.S.C. 154(b) by 0 days.

(21) Appl. No.: 09/560,708

(22) Filed: Apr. 27, 2000

(51) Int. Cl.$^7$ ................................................ A61L 9/00
(52) U.S. Cl. .......................... 422/32; 422/20; 422/21; 422/22; 422/23; 422/92; 426/230; 426/336; 426/265; 426/312
(58) Field of Search ........................ 422/32, 20, 21, 422/22, 23, 92; 426/230, 236, 312, 265

(56) References Cited

U.S. PATENT DOCUMENTS

| | | | |
|---|---|---|---|
| 3,842,521 A | 10/1974 | Faldi | 37/57 |
| 3,897,210 A | 7/1975 | Gruber et al. | 21/58 |
| 4,133,638 A | 1/1979 | Healey | 422/32 |
| 4,207,286 A | 6/1980 | Gut Boucher | 422/21 |
| 4,233,323 A | 11/1980 | Sway et al. | 426/55 |
| 4,256,574 A | 3/1981 | Bhargava | 210/614 |
| 4,517,159 A | 5/1985 | Karlson | 422/20 |
| 4,549,477 A | 10/1985 | McCabe, Jr. | 99/477 |
| 4,654,217 A | 3/1987 | Nagoshi | 426/524 |
| 4,657,758 A | 4/1987 | Goldemberg et al. | 424/49 |
| 4,689,963 A | 9/1987 | Sakai | 62/64 |
| 4,818,548 A | 4/1989 | Cheng | 426/265 |
| 4,827,727 A | 5/1989 | Caracciolo | 62/63 |
| 4,827,965 A | 5/1989 | Wates | 137/88 |
| 4,968,520 A | 11/1990 | Wang | 426/524 |
| 5,011,599 A | 4/1991 | Kearney et al. | 210/130 |
| 5,011,699 A | 4/1991 | Mitsuda et al. | 426/320 |
| 5,015,442 A | 5/1991 | Hirai | 422/121 |
| 5,053,140 A | 10/1991 | Hurst | 210/704 |
| 5,059,152 A | 10/1991 | Barber, III | 452/135 |
| 5,087,466 A | 2/1992 | Coudrains et al. | 426/256 |
| 5,135,714 A | 8/1992 | Wang | 422/23 |
| 5,184,471 A | 2/1993 | Losacco et al. | 62/63 |
| 5,213,759 A | 5/1993 | Castberg et al. | 422/22 |
| 5,227,184 A | 7/1993 | Hurst | 426/312 |
| 5,281,428 A | 1/1994 | Morgan | 426/312 |
| 5,344,622 A | 9/1994 | Faddis et al. | 422/306 |
| 5,352,467 A | 10/1994 | Mitchell et al. | 426/316 |
| 5,389,357 A | 2/1995 | Conde | 422/29 |
| 5,403,602 A | 4/1995 | Endico | 426/312 |
| 5,514,345 A | 5/1996 | Garbutt et al. | 422/124 |
| 5,597,599 A | 1/1997 | Smith et al. | 426/316 |
| 5,700,505 A | 12/1997 | Hurst | 426/312 |
| 5,703,009 A | 12/1997 | Yvin et al. | 524/116 |
| 5,756,046 A | 5/1998 | Winks et al. | 422/32 |
| 5,783,242 A | 7/1998 | Teague | 426/320 |
| 5,965,087 A | 10/1999 | Caracciolo, Jr. | 422/28 |
| 6,066,348 A | 5/2000 | Yuan et al. | 426/236 |
| 6,086,833 A | 7/2000 | Conners et al. | 422/92 |
| 6,120,822 A | 9/2000 | Denvir et al. | 426/230 |

FOREIGN PATENT DOCUMENTS

| | | |
|---|---|---|
| CA | 1 239 710 | 7/1988 |
| DE | 3209930 A1 | 9/1983 |
| EP | 0722 741 | 7/1996 |
| JP | 3-216173 | 9/1991 |
| JP | 6-153880 | 6/1994 |
| JP | 6-327448 | 11/1994 |
| JP | 7-80052 | 3/1995 |
| JP | 10-174570 | 6/1998 |
| WO | WO 00/23383 | 4/2000 |

OTHER PUBLICATIONS

James Yuan et al., contributors, Reprinted from Nov., 1998 Fresh–Cut ™ Magazine, "Biocidal Efficacy of Ozone in Processing," 3 pages.

*Primary Examiner*—Yogendra N. Gupta
*Assistant Examiner*—Derrick G Hamlin
(74) *Attorney, Agent, or Firm*—Linda K. Russell; Christopher J. Cronin

(57) ABSTRACT

A method for sanitizing a food processing environment includes the preparation of an aqueous ozone was solution for use in sanitizing food contact surfaces and food processing work stations. During preparation of an ozone wash solution, ozone off-gas is collected from the aqueous ozone solution. The ozone off-gas is then introduced into an ambient of the food processing environment. The introduction of the ozone off-gas can be carried out in conjunction with the application of the ozone wash solution to food contact surfaces. Additionally, the ozone off-gas can be introduced at relatively high concentrations for application to food processing equipment and food contact surfaces or, alternatively, the ozone off-gas can be diluted to relatively low levels for introduction into the ambient air of a food processing facility.

18 Claims, No Drawings

METHOD FOR SANITIZING A FOOD PROCESSING ENVIRONMENT

FIELD OF THE INVENTION

The present invention relates, in general, to methods for sanitizing food processing equipment and food contact surfaces and, more particularly, to food processing sanitization methods using ozone.

BACKGROUND OF THE INVENTION

Microbial outgrowth is a major cause of food spoilage. The presence of pathogenic microorganisms on food products can potentially lead to food-borne outbreaks of disease and cause significant economic loss to food processors. The need to delay the onset of spoilage has led the food processing industry to seek effective means for disinfecting food products in order to ensure food safety. Currently, food processors use several different technologies to eliminate, retard or prevent microbial outgrowth. For example, techniques such as heating, radiation and application of chemical agents are currently in use.

Microbial contamination of food products can occur not only from the product itself, but also from the environment. For example, food products are susceptible to microbial contamination during processing steps carried out after the initial sanitization process. Contamination sources from the food processing environment can include processing equipment, such as knives and mixers, food contact surfaces, such as cutting boards, conveyor belts and interior surfaces, such as floors, walls and ceilings. An additional source of contamination in the food processing environment can also be the ambient air within a food processing facility.

Current methods for sanitizing food processing areas include the use of heat or chemicals to clean floors, walls and food contact surfaces. While the use of steam or hot water can be effective, its efficiency is low on large surface areas. In addition to water, chemical sanitizers, such as chlorine and quaternary ammonium compounds are also in use. Although chemical sanitizers can be effective, there efficacy can vary with respect to different microorganisms present in a food processing environment. Additionally, chemical sanitizers are themselves toxic and they can alter the taste the food that comes in contact with a chemically sanitized surface. Further, the use of chemical sanitizers requires that the chemicals be stored near their point of use and they have safety problems associated with their storage, handling and transportation.

Ozone sanitization methods have proven to be highly effective when applied directly to food products. Ozone has been shown to be a highly reactive oxidant that is capable of destroying most cellular constituents of pathogenic microorganisms. Additionally, ozone advantageously naturally decomposes into oxygen. At low levels, ozone will decompose into oxygen within a few hours. Ozone is normally produced by irradiating an oxygen-containing gas with ultraviolet light or by corona discharge. Ozone processes have been developed using an ozone solution made by injecting ozone gas into water that is used to sanitize and disinfect food products.

While the use of ozone has proven effective at controlling microbial outgrowth on food products, the generation and use of ozone must be carefully controlled to prevent injury to food processing personnel. For example, high concentrations of ozone can be toxic to humans. The Occupational Safety and Health Administration (OSHA) specifies that ozone exposure in the workplace should not exceed 0.1 parts-per-million (ppm) for an eight hour workshift or 0.3 ppm for fifteen minutes and not to be repeated more than twice during an eight hour workshift. In order to meet OSHA requirements, ozone generation and handling systems used in the food processing industry must be properly vented to ensure that workers are not overexposed to ozone. Collecting and containing ozone gas requires expensive, carefully regulated equipment that adds significantly to the cost of food processing operations. In addition to equipment costs, the excess ozone gas must be vented, which represents a loss of an expensive process gas. While ozone sanitization methods have proven effective, improved methods of utilizing ozone for sanitizing a food processing environment are still needed.

BRIEF SUMMARY OF THE INVENTION

The present invention provides a method of sanitizing a food processing environment. In one aspect, the method includes preparing an aqueous ozone wash solution for use in sanitizing food contact surfaces and food processing workspaces. The method further provides for collecting ozone off-gas from the aqueous ozone solution. The collected ozone off-gas is then introduced into an ambient of the food processing environment. The method of the invention further includes sanitizing the food processing workspace, food storage containers and food processing equipment using the collected ozone off-gas.

In another aspect of the invention, ozone gas is directly generated and discharged into a food processing workspace. Where either directly generated ozone gas or ozone off-gas is introduced into the ambient of the food processing workspace, the ozone concentration is maintained within exposure limits specified by OSHA. For example, the ozone concentration level is maintained at about 0.05 ppm or less. Thorough circulation of ozone within the workspace ambient is provided by air distribution systems within the workspace.

In a further aspect of the invention, an ozone off-gas stream is generated to provide a constant product C·T where C is the ozone dose mg/min and T is the surface contact time in minutes. The ozone off-gas stream is produced at an ozone flow rate of about 0.1 to about 15 liters per second.

In a still further aspect of the invention, the ozone off-gas is mixed with a feed gas prior to introducing the ozone off-gas into an ambient of the food processing environment. The feed gas can be oxygen, air, a mixture of oxygen and air, a mixture of the oxygen, air and an inert gas. The inert gas can include argon, krypton, xenon, neon, carbon dioxide ($CO_2$) and nitrogen.

The invention further includes preparation of an ozone wash solution from which the off-gas is collected. The ozone solution can have an ozone concentration ranging from about 0.1 ppm to about 15 wt %.

The present invention further contemplates the use of the collected ozone off-gas or an ozone wash solution or both to disinfect food contact surfaces, interior surfaces of food processing facilities, and food processing equipment. The ozone wash solution can be prepared as a continuous stream of ozone wash solution or in batches of solution. In either method, ozone off-gas is continuously collected for use in sanitizing the food processing environment.

DETAILED DESCRIPTION OF THE PREFERRED EMBODIMENT

In the present invention, ozone gas is produced by either bombarding oxygen with ultraviolet radiation at a wavelength below about 200 nm or through the use of a corona discharge. Alternatively, an oxygen-containing gas, such as air and the like, can be used to generate ozone. The ozone generator is configured such that the generated ozone gas can be sparged into an aqueous solution for the production of an ozone wash solution.

The ozone produced by the ozone generator can be mixed with a feed gas prior to sparging the ozone into the aqueous solution. The feed gases include oxygen, air, a mixture of oxygen and air, an inert gas, a mixture of air, oxygen and the inert gas, and the like. The inert gases can be nitrogen, carbon dioxide, argon, krypton, xenon, neon and mixtures thereof. In an alternative method, the feed gas is sparged into the aqueous solution separately, rather than being mixed with ozone prior to sparging.

Preferably, the ozone sparging process is carried out in a tank into which an aqueous solution is supplied. In one embodiment, the aqueous solution is primarily water. However, the water can contain chemical agents, such as small quantities of chlorine added to city water, and the like. In a preferred process, the inert gas makes up about 10 to about 99 weight percent of the total gas sparged into the aqueous solution. The sparging process can be carried out over a wide temperature range in which the aqueous solution is maintained at a temperature below about 70° C. Ozone solution is withdrawn from the sparging apparatus having a concentration of about 0.1 ppm to about 15 wt %. In one embodiment, a continuous aqueous ozone stream is withdrawn from the sparging apparatus at a flow rate ranging from about 0.1 liters per second to about 15 liters per second. In an alternative embodiment, aqueous ozone solution is prepared in a batch system. In the batch system, many gallons of aqueous ozone solution are prepared and then transferred to ozone distribution systems within the food processing facility.

With either the continuous stream or the batch aqueous ozone method, the ozone solution is delivered throughout the food processing facility through a distribution system, such as piping systems and the like. At the various point-of-use locations, the ozone can be applied to interior surfaces, food contact surfaces and process equipment by means of spray nozzles, misting devices and the like.

In accordance with the invention, a vapor collection device is provided within the ozone sparging apparatus to collect ozone vapor as an off-gas from the aqueous solution. In the preparation of an aqueous ozone solution, considerable ozone can be lost because of the relative solubility of ozone. The off-gassing of ozone from the aqueous solution represents an ozone loss mechanism in the aqueous ozone preparation process. In accordance with the invention, the existing ozone loss mechanism is advantageously employed to provide a source of gaseous ozone for sanitizing a food processing environment.

In one embodiment of the invention, the collected ozone off-gas is used to produce a continuous gaseous ozone stream that is subsequently distributed to points-of-use throughout a food processing environment. The gaseous ozone stream is provided at a flow rate varying from about 0.1 liters per second to about 15 liters per second. For application of the ozone off-gas to processing equipment and food contact surfaces, the ozone concentration can vary from about 0.1 ppm to about 15 wt %. Correspondingly, where the ozone off-gas stream is to be introduced into the air within a workspace, the ozone concentration is regulated to within OSHA standards. To ensure worker safety, the ozone concentration is regulated in conjunction with the air distribution systems within the workplace to ensure that the ozone concentration within the workspace does not exceed a safe level. For example, current OSHA standards require that the ozone level not exceed 0.1 ppm for an eight hour workshift. This limit can be met by, for example, limiting the ozone concentration to a range of preferably no more than about 0.10 ppm and more preferably about 0.02 ppm to about 0.05 ppm. The ozone off-gas can be diluted to within a desired concentration range by mixing the ozone off-gas with a feed gas. In a present embodiment, any of the previously described feed gases can be mixed with the ozone off-gas prior to introduction into a workspace.

Where the ozone off-gas is to be introduced into a food storage ambient, such as food storage container, and the like, the ozone concentration can exceed workspace limits. For example, the ozone concentration can be similar to that used to sanitize food contact surfaces and processing equipment.

Without further elaboration, it is believed that one skilled in the art can, using the preceding description, utilize the invention to its fullest extent. The following specific embodiments are, therefore, to be construed as merely to illustrate and not to limit the remainder of the disclosure in any way whatsoever.

EXAMPLE I

To illustrate the effectiveness of an ozone wash solution on food contact surfaces, an aqueous ozone solution was prepared by injecting gaseous ozone into a tank of water having a 550 liter capacity. The water temperature was maintained at about 0° C. to about 4° C. The dissolved ozone concentration was controlled at about 2 ppm and monitored by a model 499A OZ ozone sensor available from Rosemont Analytical Company, California. A spray hose and shower head, coupled to the 550 liter tank, provided a means for applying the aqueous ozone solution. A cutting board was placed on top of a mobile stainless cart near 550 liter tank. The workstation and a cutting knife were rinsed with ozone solution and a fish was also rinsed with ozone solution and placed on the cutting board. The knife was used to fillet the fish on the cutting board. After filleting the fish, the knife and cutting board were again rinsed with ozone solution. After each rinse step, a swab of the cutting board was made in an area of about 2 cm by 25 cm. Additionally, 25 gram samples of a filleted fish were also collected. The preceding process was repeated with a series of fish. Additionally, as a control, the foregoing process was carried out with tap water rather than ozone solution. The 25 gram fish samples were homogenized in about 90 milliliters of deionized water and each sample was then serially diluted. A one milliliter sample of each dilution was placed on an APC Petrifilm™ available from 3M Company, Minnesota. The APC Petrifilm™ plates were incubated for about 48 hours at about 35° C. After incubation, the colonies were counted as colony forming units (CFU) per gram for the fish samples and CFU per 50 $cm^2$ for the swab samples. The bacteria counts made for the sequential processing of three fish using both the ozone solution and the controlled tap water rinse are shown in Table I.

TABLE I

Total viable microorganisms (CFU/50 cm$^2$) on cutting board after cutting white fish and rinse with ozone or control (tap water).

| TREATMENT | CONTROL | OZONE |
|---|---|---|
| Before cutting fish | 15 | 38.5 |
| After cutting the 1$^{st}$ fish | 310 | 4.0 |
| After cutting the 2$^{nd}$ fish | 193 | 13.5 |
| After cutting the 3$^{rd}$ fish | 301.5 | 4.5 |

As indicated in Table I, the bacteria count continued to build for the control samples, whereas the ozone solution rinse is shown to maintain bacteria count at a relatively low level. While the tap water rinse may prevent microbial build-up beyond some relatively high level, the tap water does not reduce the bacteria load over time. In contrast, when the ozone is applied to the cutting board, bacterial load is kept at a relatively low level and can even be reduced. The experimental results indicate that, on average, the use of ozonated water to rinse the cutting board improves the surface microbial quality by about 97%.

The effectiveness of directly contacting food products with the ozone solution is illustrated in Table II. The fish fillets were rinsed with either ozone solution or the controlled tap water. Each bacteria count shown in Table II represents the average of two sides of a fillet from the same fish.

TABLE II

Total viable microorganisms (CFU/g) on fish fillet. Fish fillets were either cut on the cutting board rinsed with ozonated water or control (tap water). Each data point represented average of 2 sides of fillets from the same fish.

| TREATMENT | CONTROL | OZONE |
|---|---|---|
| The 1$^{st}$ fish | 110.5 | 106 |
| The 2$^{nd}$ fish | 123.5 | 97 |
| The 3$^{rd}$ fish | 116.2 | 80.7 |

The results shown in Table II illustrate the effectiveness of maintaining low bacterial counts on food contact surfaces. Once a food contact surface becomes loaded with microorganisms, cross-contamination from food contact surfaces to the food itself can occur. Thus, food product quality can be directed affected by the presence of microbial load on food contact surfaces. The results shown in Table II indicate that the microbial quality of the fish was improved over time using the ozone solution, whereas the tap water control does not show an improved microbial quality with successive fish.

EXAMPLE II

During the experiment described in EXAMPLE I, the floor was periodically rinsed with the ozone solution. The microbial load on the floor was examined by swabbing a 2 cm×25 cm section of the floor after each rinsing step described above. The bacteria counts taken from two successive swabs are shown in Table III.

TABLE III

Total viable microorganisms (CFU/50 cm$^2$) on floor before and after rinsed with ozonated water at 2 ppm level.

| SWAB SAMPLE # | BEFORE RINSE | AFTER RINSE |
|---|---|---|
| 1 | 116.5 | 0 |
| 2 | 193.5 | 0 |

The floor bacteria counts taken before and after rinsing with ozone solution show almost a complete removal of bacteria from the floor surface.

EXAMPLE III

To illustrate the effectiveness of introducing gaseous ozone into a workspace to control airborne bacteria, the air quality within the experimental lab was analyzed with and without the introduction of ozone into the laboratory ambient air. To introduce ozone into the laboratory ambient, an ozone generator (AZCOZON, AZCO Industries, Ltd., Surrey, B.C., Canada) was placed in the center of the laboratory and ozone was continuously produced into the air at a concentration of about 0.01 ppm to 0.03 ppm. Additionally, three fans were placed at different angles within the laboratory to maintain proper air circulation. The dimensions of the laboratory was about 1400 square feet and the static laboratory air volume was about 18200 cubic feet. At the end of about an eight hour exposure time, the laboratory air was sampled using a Millipore Air T™ air tester available from Millipore Corporation, Bedford, Mass. The ozone was circulated while processing food according to the previous experiments described above. At the end of approximately an eight hour workshift, duplicate samples were taken over a five day period. The experiment was repeated by taking air samples in the same laboratory over a five day period without introducing ozone into the laboratory air ambient. For both the ozone introduction and the normal air sampling, duplicate samples were taken at each sampling. The results are shown in Table IV.

TABLE IV

Total viable air-borne microorganisms (CFU/1000 L) before and after treated with ozone at 0.01–0.03 ppm level.

| SAMPLING DAY | WEEK 1 (CONTROL) | | WEEK 2 (OZONE) | |
|---|---|---|---|---|
| | SAMPLE #1 | SAMPLE #2 | SAMPLE #1 | SAMPLE #2 |
| 1 | 15 | 16 | 13 | 15 |
| 2 | 22 | 34 | 7 | 10 |
| 3 | 12 | 13 | 3 | 5 |
| 4 | 14 | 24 | 2 | 5 |
| 5 | 4 | 9 | 1 | 1 |

The results show a fluctuation in bacterial count over the five day sampling period. On four of the five days, the ozone samples show a reduced bacteria count compared with the controlled sample. Additionally, the ozonated air shows a continual reduction in bacteria count over the five day period, whereas the control samples do not show a steady reduction in bacteria levels.

Thus, it is apparent that there has been described, in accordance with the invention, a method for sanitizing a food processing environment that fully meets the advantages set forth above. Although the invention has been described and illustrated with reference to specific illustrative embodiments thereof, it is not intended that the invention be limited to those illustrative embodiments. Those skilled in the art will recognize that variations and modifications can be made without departing from the spirit of the invention. For example, various chemicals can be added to the ozone wash solution to enhance its bactericidal effectiveness. Additionally, the pH of the solution can be adjusted to a desired level as needed. It is therefore intended to include within the invention all such variations and modifications as fall within the scope of the appended claims and equivalents thereof.

What is claimed is:

1. Method of sanitizing food processing environment comprising: preparing an aqueous ozone wash solution for use in sanitizing food contact surfaces and food processing workspaces;

collecting ozone off-gas from the aqueous ozone solution; and introducing the ozone off-gas into an ambient of the food processing environment.

2. The method of claim 1, wherein introducing the ozone off-gas into an ambient of the food processing environment comprises introducing the ozone off-gas into an ambient selected from the group consisting of a food processing workspace, a food storage container and a combination of both.

3. The method of claim 1, wherein the ozone off-gas is introduced into an ambient of the food processing environment at a concentration level of no more than about 0.10 ppm.

4. The method of claim 3, wherein the ozone off-gas is introduced at a concentration level of about 0.02 ppm to about 0.05 ppm.

5. The method of claim 1 further comprising circulating the ozone off-gas within the ambient of the food processing environment.

6. The method of claim 1, wherein introducing the ozone off-gas into an ambient of the food processing environment comprises producing an ozone off-gas stream at a constant C·T, where C is the ozone dose mg/min and T is the surface contact time in minutes.

7. The method of claim 1, wherein preparing an aqueous ozone solution comprises preparing an ozone solution having an ozone concentration of about 0.1 ppm to about 15 wt. %.

8. The method of claim 1, wherein introducing the ozone off-gas into an ambient of the food processing environment comprises forming an ozone flow rate of about 0.1 to about 15 liters per second.

9. The method of claim 1 further comprising mixing the ozone off-gas with a feed gas prior to introducing the ozone off-gas into an ambient of the food processing environment.

10. The method of claim 9 wherein the feed gas comprises a gas selected from the group consisting of oxygen, air, a mixture of oxygen and air, an inert gas and a mixture of oxygen, air and an inert gas.

11. The method of claim 10, wherein the inert gas is selected from the group consisting of Ar, Kr, Xe, Ne, $CO_2$ and $NO_2$.

12. The method of claim 9, wherein the feed gas comprises an inert gas selected from the group consisting of Ar, Kr, Xe, Ne, $CO_2$ and $NO_2$.

13. A method for sanitizing a food processing environment comprising:

preparing an ozone wash solution and collecting ozone off-gas from the solution;

applying the ozone wash solution to food contact surfaces; and introducing the ozone off-gas into an ambient of the food processing environment.

14. The method of claim 13, wherein preparing an ozone wash solution comprises preparing an aqueous ozone solution having an ozone concentration of about 0.1 ppm to about 15 wt. %.

15. The method of claim 13, wherein preparing an ozone wash solution comprises producing a continuous stream of ozone wash solution at a flow rate of about 0.1 liter/sec to about 15 liter/sec.

16. The method of claim 13, wherein preparing an ozone wash solution comprises preparing a batch solution.

17. The method of claim 13, wherein applying the ozone wash solution to food contact surfaces comprises applying the ozone wash solution to food processing equipment.

18. The method of claim 13 further comprising applying the ozone wash solution to food processing room interior surfaces.

* * * * *